(12) United States Patent
Yu et al.

(10) Patent No.: US 6,923,772 B2
(45) Date of Patent: Aug. 2, 2005

(54) APPARATUS AND METHOD FOR DETERMINING RESPONDERS TO CARDIAC RESYNCHRONIZATION THERAPY USING IMPLANTABLE ACCELEROMETERS

(75) Inventors: Yinghong Yu, Maplewood, MN (US); Jiang Ding, Maplewood, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 475 days.

(21) Appl. No.: 10/236,714

(22) Filed: Sep. 6, 2002

(65) Prior Publication Data

US 2004/0049112 A1 Mar. 11, 2004

(51) Int. Cl.$^7$ .................................................. A61B 5/02
(52) U.S. Cl. ............................. 600/508; 600/481; 607/9
(58) Field of Search ................................. 600/373–375, 600/481–486, 508–528; 607/5, 6, 9, 17, 119, 122, 123

(56) References Cited

U.S. PATENT DOCUMENTS

| 5,496,361 | A | * | 3/1996 | Moberg et al. ............. 607/122 |
| 6,197,610 | B1 | | 3/2001 | Toda |
| 6,766,189 | B2 | * | 7/2004 | Yu et al. ..................... 600/510 |
| 2002/0143264 | A1 | * | 10/2002 | Ding et al. ................. 600/510 |
| 2003/0176896 | A1 | * | 9/2003 | Lincoln et al. .............. 607/18 |

OTHER PUBLICATIONS

NASPE Abstract No. 773; *Evaluation of Variation in Wall Motion by Multisite Pacing with a New Fiberoptical Sensing System*; Axel Kloppe, Axel Prenger–Berninghoff, Stefan Mueller, Joern Weckmueller, Martin Hexamer, and Juergen Werner. Biomed Engineering, Bochum, Germany.

* cited by examiner

*Primary Examiner*—Robert L. Nasser
*Assistant Examiner*—Patricia Mallari
(74) *Attorney, Agent, or Firm*—Merchant & Gould P.C.

(57) ABSTRACT

A device for measuring a synchronicity of contraction of a heart to determine if an individual would be a responder to cardiac resynchronization therapy. The device may include a first electrode positioned at a first ventricular wall location to measure movement of the first ventricular wall location and generate a first signal, as well as a second electrode positioned at a second ventricular wall location to measure movement of the second ventricular wall location and generate a second signal. A processing module may process the first and second signals, for example, integrate the signals multiple times, and generate an output based on the processed signals. Based on this output, an individual can be labeled a responder or non-responder to cardiac resynchronization therapy. The electrodes may each include an accelerometer to measure acceleration of the heart wall.

18 Claims, 8 Drawing Sheets

APPARATUS AND METHOD FOR DETERMINING RESPONDERS TO CARDIAC RESYNCHRONIZATION THERAPY USING IMPLANTABLE ACCELEROMETERS

TECHNICAL FIELD

The present invention is directed to cardiac resynchronization systems. More specifically, the present invention is directed to systems and methods that employ mechanical measurement of cardiac wall motion to determine whether an individual would be a responder to cardiac resynchronization therapy.

BACKGROUND

Figure 1:
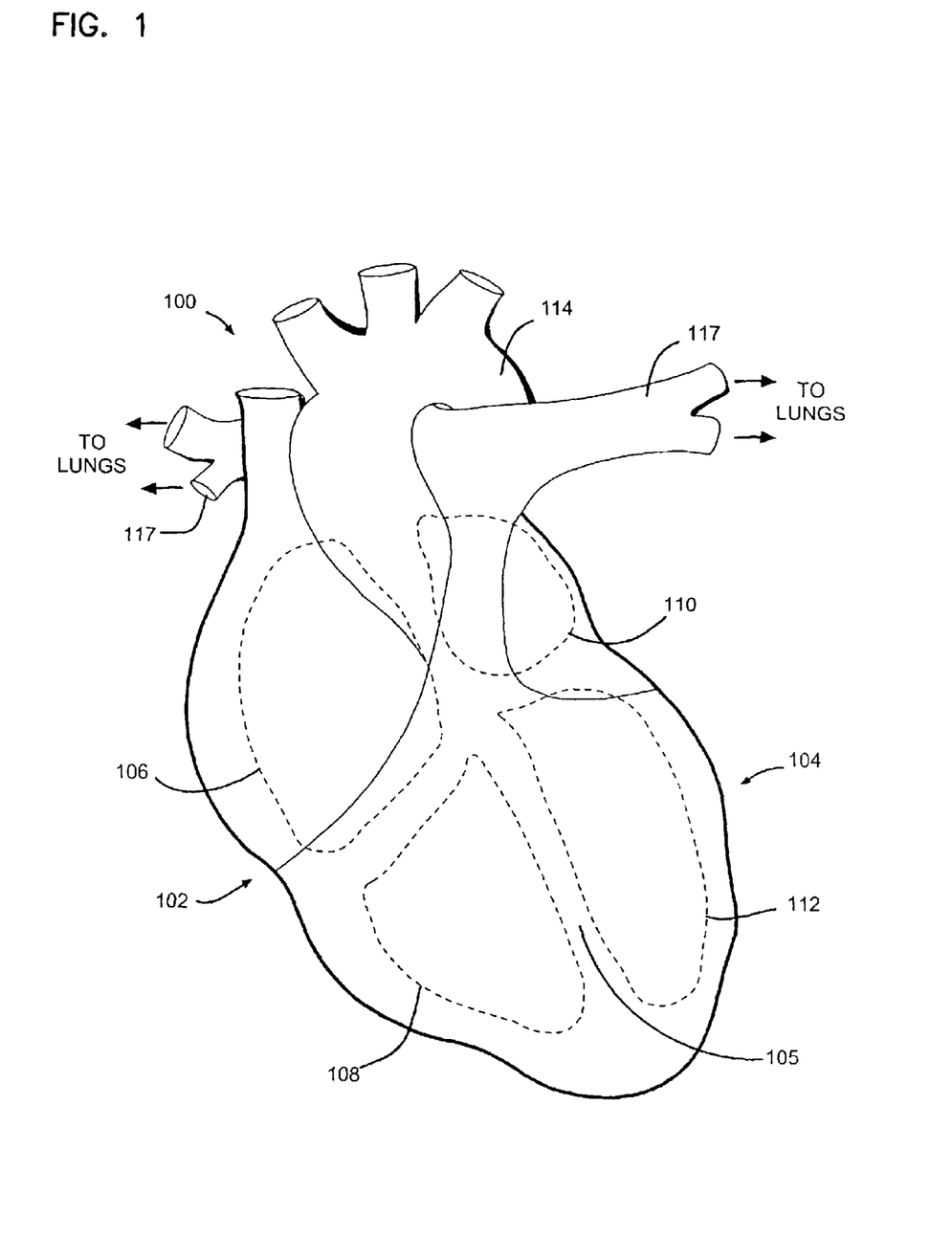
FIG. 1 is a simplified illustration depicting primary pumping components of a human heart.

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112 separated by an interventricular septum 105. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 1117. Within the lungs, waste products such as carbon dioxide are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. After the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase, or systole, the ventricular muscle cells of the right and left ventricles 108 and 112 contract to pump blood through the pulmonary circulation and throughout the body, respectively. Conversely, during the diastolic phase, or diastole, the ventricular muscle cells of the right and left ventricles 108 and 112 relax, during which the right and left atriums 106 and 110 contract to force blood into the right and left ventricles 108 and 112, respectively. Typically, the cardiac cycle occurs at a frequency between 60 and 100 cycles per minute and can vary depending on physical exertion and/or emotional stimuli, such as pain or anger.

Figure 2:
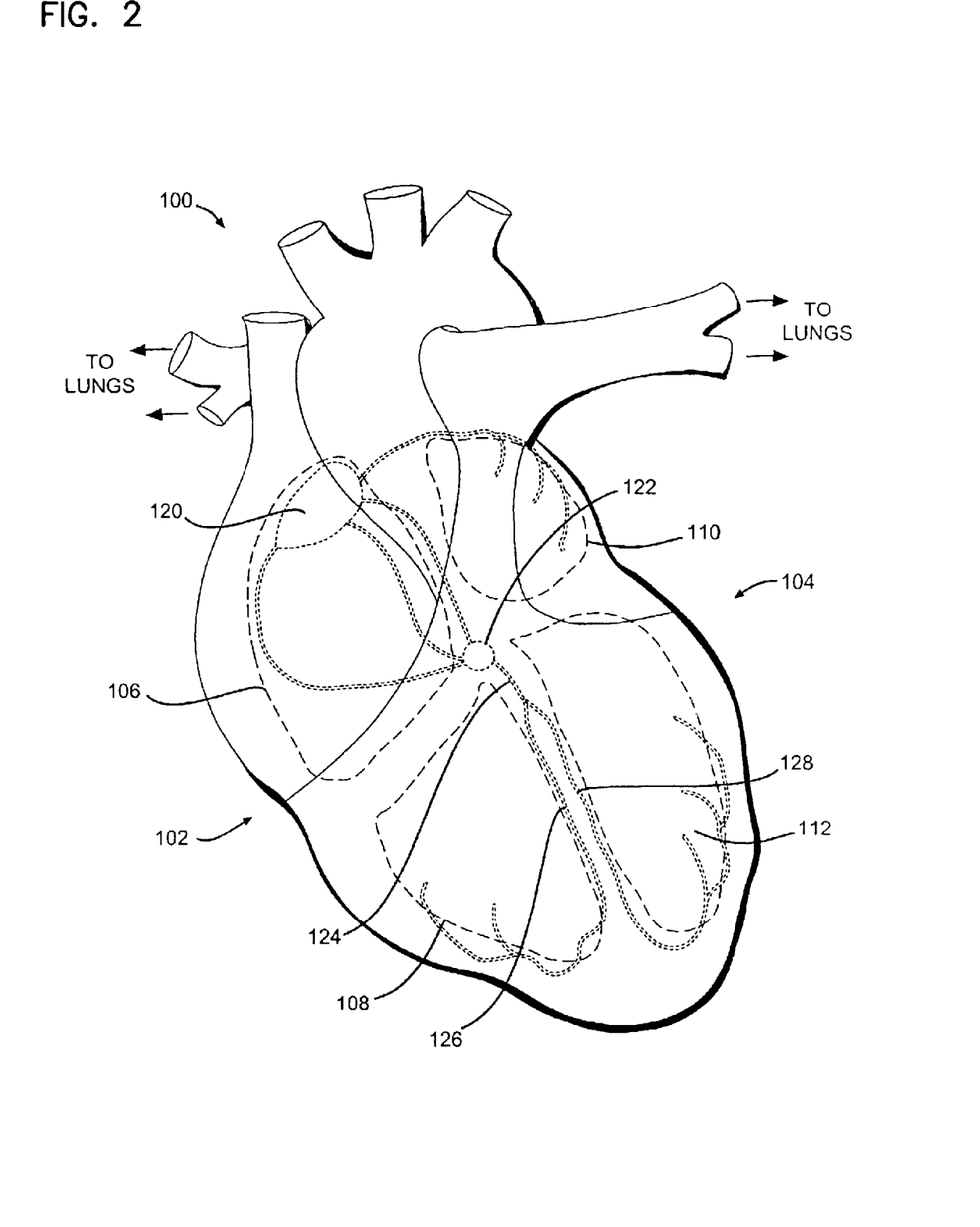
FIG. 2 is a simplified illustration depicting a human heart and the transmission paths over which a normal heart provides depolarization waves to the heart chambers.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (the sinoatrial node) and a ventricular node 122 (the atrioventricular node). The sinoatrial node 120 initiates an electrical impulse that spreads through the muscle tissues of the right and left atriums 106 and 110 and the atrioventricular node 122. As a result, the right and left atriums 106 and 110 contract to pump blood into the right and left ventricles 108 and 112, as discussed above.

At the atrioventricular node 122, the electrical signal is momentarily delayed before propagating through the right and left ventricles 108 and 112. Within the right and left ventricles 108 and 112, the conduction system includes right and left bundle branches 126 and 128 that extend from the atrioventricular node 122 via the Bundle of His 124. The electrical impulse spreads through the muscle tissues of the right and left ventricles 108 and 112 via the right and left bundle branches 126 and 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106 and 110 contract and relax synchronously. Shortly after the atrial contractions, both the right and left ventricles 108 and 112 contract and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relaxation and filling. In situations where the blockage is in the ventricles (e.g., the right and left bundle branches 126 and 128), the right and/or left ventricles 108 and 112 can only be excited through slow muscle tissue conduction. As a result, the muscular walls of the affected ventricle (108 and/or 112) do not contract synchronously (known as asynchronous contraction), thereby reducing the overall effectiveness of the heart 100 to pump oxygen-rich blood throughout the body.

Various medical procedures have been developed to address these and other heart disorders. In particular, cardiac resynchronization therapy ("CRT") can be used to improve the conduction pattern and sequence of the heart 100. CRT involves the use of an artificial electrical stimulator that is surgically implanted within the patient's body. Leads from the stimulator can be affixed at a desired location within the heart 100 to effectuate synchronous atrial and/or ventricular contractions. Typically, the location of the leads, or the stimulation site, is selected based upon the severity and/or location of the blockage. Electrical stimulation signals can be delivered to resynchronize the heart, thereby improving cardiac performance.

In a clinical setting, an individual may exhibit one or more of the heart abnormalities noted above. A practitioner is faced with correctly diagnosing and treating the individual's heart abnormalities. Correctly identifying patients with abnormal ventricular contraction patterns is a key to the successful application of CRT. For example, results from clinical studies have shown that hemodynamic response to CRT typically varies from patient to patient, ranging from very positive (i.e. an improvement) to substantially negative (i.e. deterioration). Patients that may benefit from CRT are labeled responders, while patients who may not are labeled non-responders.

Thus, in order to predict the benefit of CRT for a particular patient, the patient typically must be screened prior to determining whether the patient is a responder to the therapy. There are several methods that are used to screen possible responders to CRT from non-responders. For example, one common method that attempts to predict hemodynamic response to CRT relies on measurement of the QRS complex width as measured using a surface electrocardiogram (ECG). Other methods include measuring the pressure within the ventricles and then analyzing the pressure data to separate responders from non-responders. However, these known methods can be inaccurate because none of the methods measure the actual movement of the heart walls in an attempt to measure synchronicity of the contractions of the heart.

Therefore, there is a need for systems that can measure direct mechanical motion of a patient's heart walls to determine whether the patient would be a responder to CRT.

SUMMARY

Embodiments of the present invention can be used to determine the synchronization of atrial and/or ventricular wall contraction by employing direct mechanical measurement. The direct mechanical measurement of various heart wall motions can be accomplished using accelerometers positioned within or near the walls. Signals from these accelerometers can be processed and compared to determine the degree of synchronization. Based on these measurements, a patient can be labeled a responder or non-responder to cardiac resynchronization therapy. Further, if a device embodying the present invention is implanted, the device may initiate and terminate cardiac resynchronization therapy as a patient's needs change.

In one aspect, the invention relates to a device for measuring a synchronicity of contraction of a heart to determine if an individual would be a responder to cardiac resynchronization therapy. The device may include a first electrode positioned at a first ventricular wall location and configured to mechanically measure movement of the first ventricular wall location, a second electrode positioned at a second ventricular wall location and configured to mechanically measure movement of the second ventricular wall location, a processing module coupled to the first and second electrodes, the processing module adapted to process a first signal produced by the first electrode at the first ventricular wall location and a second signal produced by the second electrode at the second ventricular wall location and generate an output based on the processed signals, and a comparator module coupled to the processing module to indicate that the individual would be a responder if the output of the processing module exceeds a threshold and to indicate that the individual would be a non-responder if the output of the processing module is below the threshold.

In another aspect, the invention relates to a device for determining whether an individual would be a responder to cardiac resynchronization therapy, including a first accelerometer positioned at a first ventricular wall location, a second accelerometer positioned at a second ventricular wall location, a processing module coupled to the first and second accelerometers, the processing module adapted to process a first signal produced by acceleration of the first accelerometer at the first ventricular wall location and a second signal produced by acceleration of the second accelerometer at the second ventricular wall location and generate an output, and a comparator module coupled to the processing module to indicate that the individual would be a responder if the output of the processing module exceeds a threshold and to indicate that the individual would be a non-responder if the output of the processing module is below the threshold.

In yet another aspect, the invention relates to a cardiac resynchronization system including a cardiac resynchronization device coupled to a heart of an individual to provide cardiac resynchronization therapy and a device coupled to the cardiac resynchronization device. The device may include a first accelerometer positioned at a first ventricular wall location, a second accelerometer positioned at a second ventricular wall location, a processing module coupled to the first and second accelerometers, the processing module adapted to process a first signal produced by acceleration of the first accelerometer at the first ventricular wall location and a second signal produced by acceleration of the second accelerometer at the second ventricular wall location and generate an output, and a comparator module coupled to the processing module to indicate that the individual would be a responder if the output of the processing module exceeds a threshold and to indicate that the individual would be a non-responder if the output of the processing module is below the threshold.

In another aspect, the invention relates to a method for determining whether an individual would be a responder to cardiac resynchronization therapy, the method including steps of: sensing acceleration with a first accelerometer located at a first location on the individual's heart to produce a first signal; sensing acceleration with a second accelerometer located at a second location on the heart to produce a second signal; processing the first signal and the second signal to create a synchronicity index that measures a phase difference of contraction at the first and second locations; and comparing the synchronicity index to a threshold to determine whether an individual would be a responder.

In another aspect, the invention relates to a device for determining whether an individual's heart would be a responder to cardiac resynchronization therapy including a first accelerometer means for measuring acceleration of the heart at a first ventricular wall location and for producing a first signal, a second accelerometer means for measuring acceleration of the heart at a second ventricular wall location and for producing a second signal, a processing means for processing the first signal and the second signal and generating an output, and a comparator means for indicating whether the individual would be a responder or a non-responder based on the output from the processing means.

In yet another aspect, the invention relates to a computer-readable medium having computer-executable modules including a processing module adapted to process a first signal produced by acceleration of a first accelerometer at a first ventricular wall location and a second signal produced by acceleration of a second accelerometer at the second ventricular wall location and generate an output, and a comparator module coupled to the processing module to generate a signal indicating that the individual would be a responder if the output of the processing module exceeds a threshold and indicating that the individual would be a non-responder if the output of the processing module is below the threshold.

DETAILED DESCRIPTION

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

Embodiments of the present invention can be used to determine whether an individual would be a responder (i.e. benefit) or would be a non-responder (i.e. not benefit) to cardiac resynchronization therapy (CRT). Example embodiments may utilize one or more devices to mechanically measure contraction of the walls of the heart and thereby determine the synchronicity of those heart contractions.

In one example embodiment, accelerometers can be placed within electrode leads routed to various atrial or ventricular wall locations of a heart. The accelerometers can provide signals corresponding to direct mechanical measurement of the movement of the cardiac walls. Embodiments of the present invention can process the signals from the accelerometers and determine whether a patient should be labeled as a responder or a non-responder to CRT.

Figure 3:
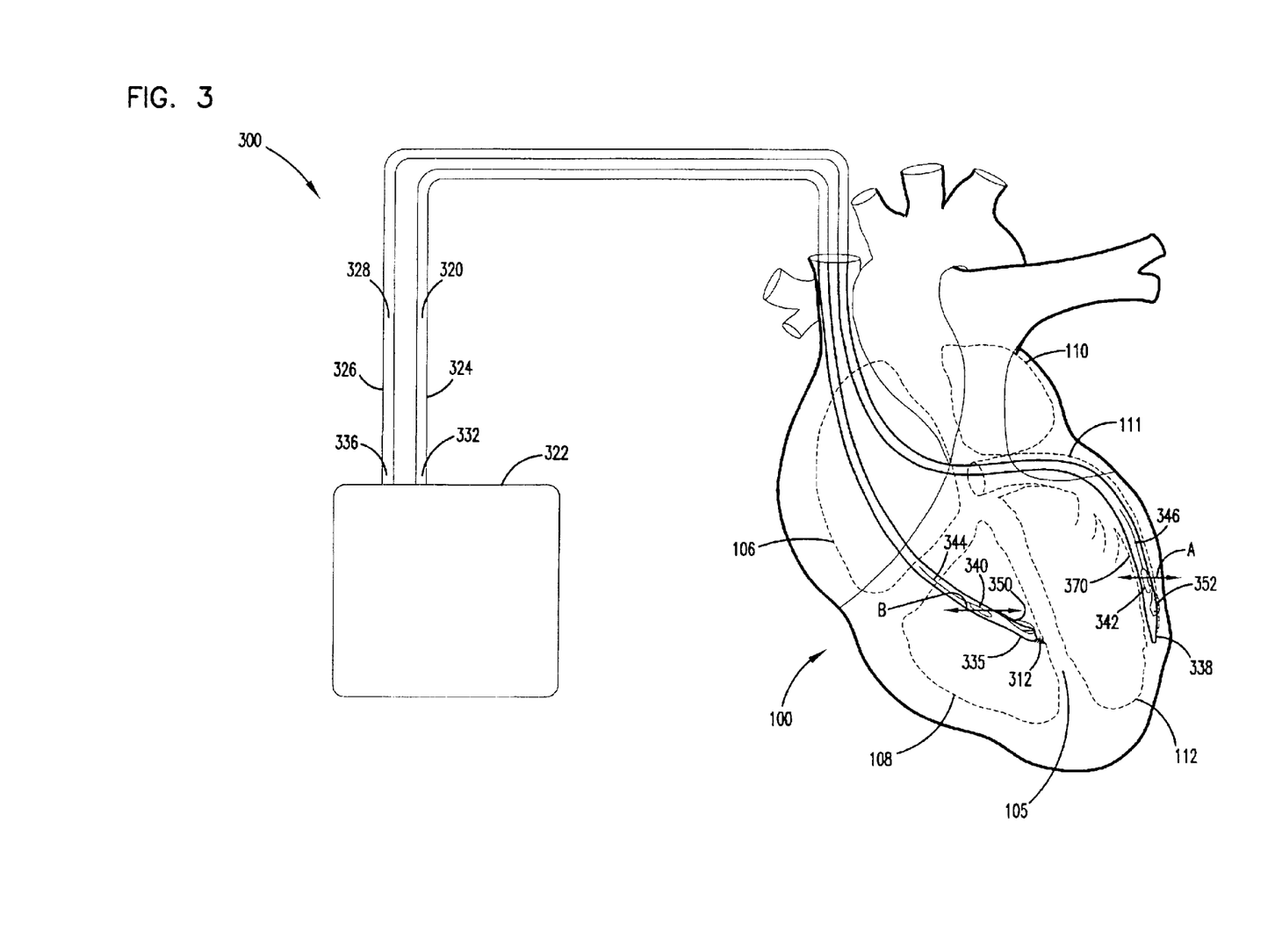
FIG. 3 is a simplified illustration depicting an example embodiment of a device according to the present invention coupled to a human heart.

As shown in FIG. 3, an example device 300 made in accordance with the present invention generally includes a control unit 322 and implantable leads 324 and 326 coupled to the unit 322. The leads 324 and 326 are, in turn, introduced into the heart 100, as described below. As also described in more detail below, the unit 322 may be implanted or may be used as an external device.

The implantable leads 324 and 326 may comprise elongate bodies, both having a proximal end 332 and 336, respectively, and a distal end 335 and 338, respectively. The implantable leads 324 and 326 may include one or more acceleration sensor units 344 and 346, respectively, and may further include one or more pacing/sensing electrodes 350 and 352, respectively. The electrodes 350 and 352 can be used to sense electrical activity or provide electrical stimulation to the heart tissue adjacent to the electrodes.

Each lead 324 and 326 has an inner lumen 320 and 328, and the acceleration sensor units 344 and 346 may be positioned within the lumens 320 and 328 of each lead. A suitable lead for this purpose is the EasyTrak from Guidant Corporation. Suitable miniaturized accelerometers having a diameter of approximately 1 millimeter are available from Ball Semiconductor Inc. (see U.S. Pat. No. 6,197,610) and others, and these miniaturized accelerometers may be positioned within the inner lumen of the EasyTrak lead and positioned adjacent the lead's electrode after the lead has been properly positioned on or within the heart 100. The accelerometer(s) may be positioned in the lumen of the lead within the coronary sinus vein, if desired, thereby minimizing the invasiveness of the accelerometer implantation.

One method of positioning the leads 324 and 326 on or within the heart 100 includes passing the lead 326 through a vein into the right atrium chamber 106 of the heart 100, into the coronary sinus 111, and then inferiorly in the great cardiac vein in a basal region to extend the electrode 352 located at the distal end 338 onto the cardiac wall alongside the left atrium chamber 110 of the heart 100. The implantable lead 326 is then extended further into the coronary sinus 111 and anterior and/or lateral veins extending therefrom to extend the electrode 352 located at the distal end 338 onto the cardiac wall alongside the left ventricle chamber 112 of the heart 100. In one embodiment, the implantable lead 326 is fixed in place by a distal fixation mechanism 370 comprising a plurality of fixation tines that are well known in the art. When the implantable lead 326 is positioned as desired, the acceleration sensor unit 346 is passed through the inner lumen 328 of the implantable lead 326 to extend the cardiac motion sensor 342, such as an accelerometer, of the acceleration sensor unit 346 alongside the left ventricle chamber 112 of the heart 100.

In a similar manner, the implantable lead 324 may be passed into the right atrium chamber 106 of the heart 100 and through the tricuspid valve into the right ventricle 108, where the electrode 350, located at the distal end 335, is fixed in place in the interventricular septum 105 by a distal attachment mechanism 312. The distal attachment mechanism 312 may be a wire shaped into a helical cork-screw like projection, a plurality of fixation tines projecting away from the peripheral surface of the implantable lead 324, or other known structures for attaching the lead 324. Such distal attachment mechanisms are well known in the art and are intended to embed the distal end of the lead 324 in the tissue of the heart. When the implantable lead 324 is fixed in place, an acceleration sensor unit 344 is passed through the inner lumen 320 of the implantable lead 324 to extend the cardiac motion sensor 340 located at the distal end of the acceleration sensor unit 344 to the interventricular septum 105.

The method described for placing the leads 324 and 326 into the heart 100 is only one example method. Other methods for the delivery of the leads 324 and 326 are also possible. For example, a thoracotomy or trans-septal approach into the left ventricular chamber are also possible. In addition, it is possible to place the leads in different positions within the heart, or, alternatively, to utilize more than two leads including more than two acceleration sensor units. For example, an additional lead including an additional acceleration sensor unit may be placed adjacent to or coupled to the free wall of the right ventricle 108 to measure the displacement of the right ventricular free wall. Atrial wall placement may also be used.

The acceleration sensor units 344 and 346, placed in this manner, move with the corresponding ventricular wall location during contraction, as generally indicated by the arrows A and B in FIG. 3. The acceleration sensor units 344 and 346 produce signals corresponding to the acceleration, or speed of contraction, of the portion of the heart muscle at which each unit is located. The signals from the acceleration sensor units 344 and 346 are transferred to the control unit 322 via the leads 324 and 326.

Figure 4:
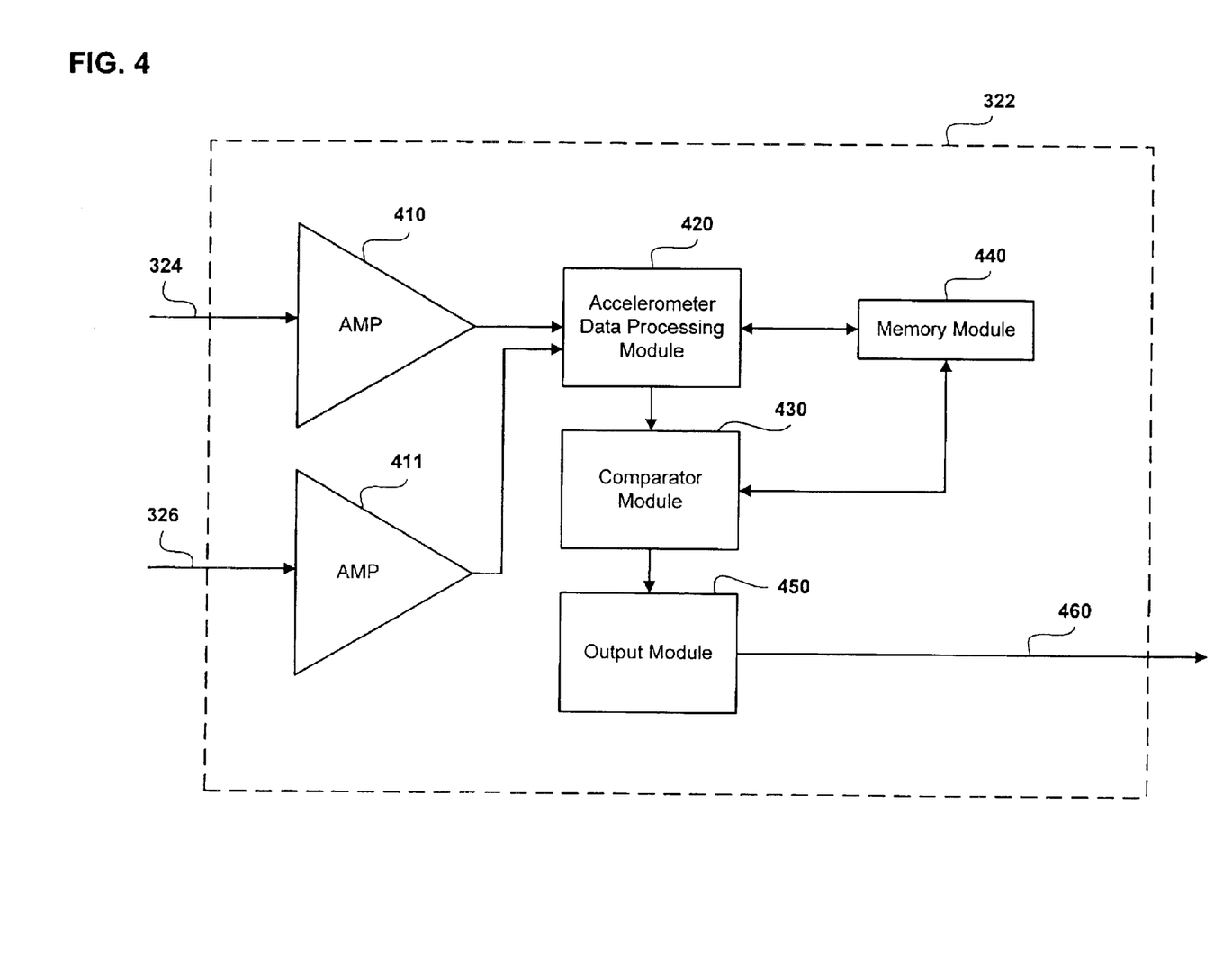
FIG. 4 is a block diagram depicting the primary components of the device shown in FIG. 3.

Referring now to FIG. 4, the control unit 322 is shown in greater detail. The unit 322 may include several submodules that process the signals generated by the acceleration sensor units 344 and 346. These submodules generally include one or more accelerometer amplifiers 410 and 411, an accelerometer data processing module 420, a comparator module 430, a memory module 440, and an output module 450 with an output 460.

The leads 324 and 326 from the acceleration sensor units 344 and 346 are coupled to the accelerometer amplifiers 410 and 411. The amplifiers 410 and 411 enhance the signals received from the accelerometers positioned at the various heart locations to improve the signal to noise ratio and provide a signal level and shape acceptable for the accelerometer data processing module 420.

The accelerometer data processing module 420 performs the bulk of the processing of the signals from the acceleration sensor units 344 and 346. The processing module 420, described in greater detail with reference to FIG. 5, generally performs the following functions: (1) identification of individual heart contractions; (2) multiple integration of the data from the acceleration sensor units to provide displacement data; (3) plotting of a displacement loop; (4) normalization of this displacement loop; and (5) creation of a synchronicity index to quantify the level of synchronization between the different portions of the heart measured.

The data processing module 420 is coupled to the comparator module 430. The comparator module 430 receives the output of the data processing module 420 and compares it to a threshold set to segregate possible responders to CRT from non-responders. This threshold may be identified clinically and could be a value above which individuals would be considered to be responders and equal to or below which individuals would be considered to be non-responders.

The accelerometer data processing module 420 and/or the comparator module 430 can be coupled to the memory module 440. The memory module 440 is any memory generally known in the art that can record and retrieve data measured from the heart and processed by the modules 420 and 430.

The comparator module 430 is coupled to the output module 450. The output module 450 receives the output of the comparator module 430 and presents it to the practitioner, or alternatively, to a CRT device implanted in the individual. For example, the output 460 of the output module 450 may be connected to a computer that manipulates or records the data from the output module 450. Also, the output 460 could simply be coupled to a display device that would indicate to a practitioner whether the individual is a responder. Alternatively, the output 460 may be coupled to a CRT device, as is shown and described with reference to FIG. 8.

Figure 5:
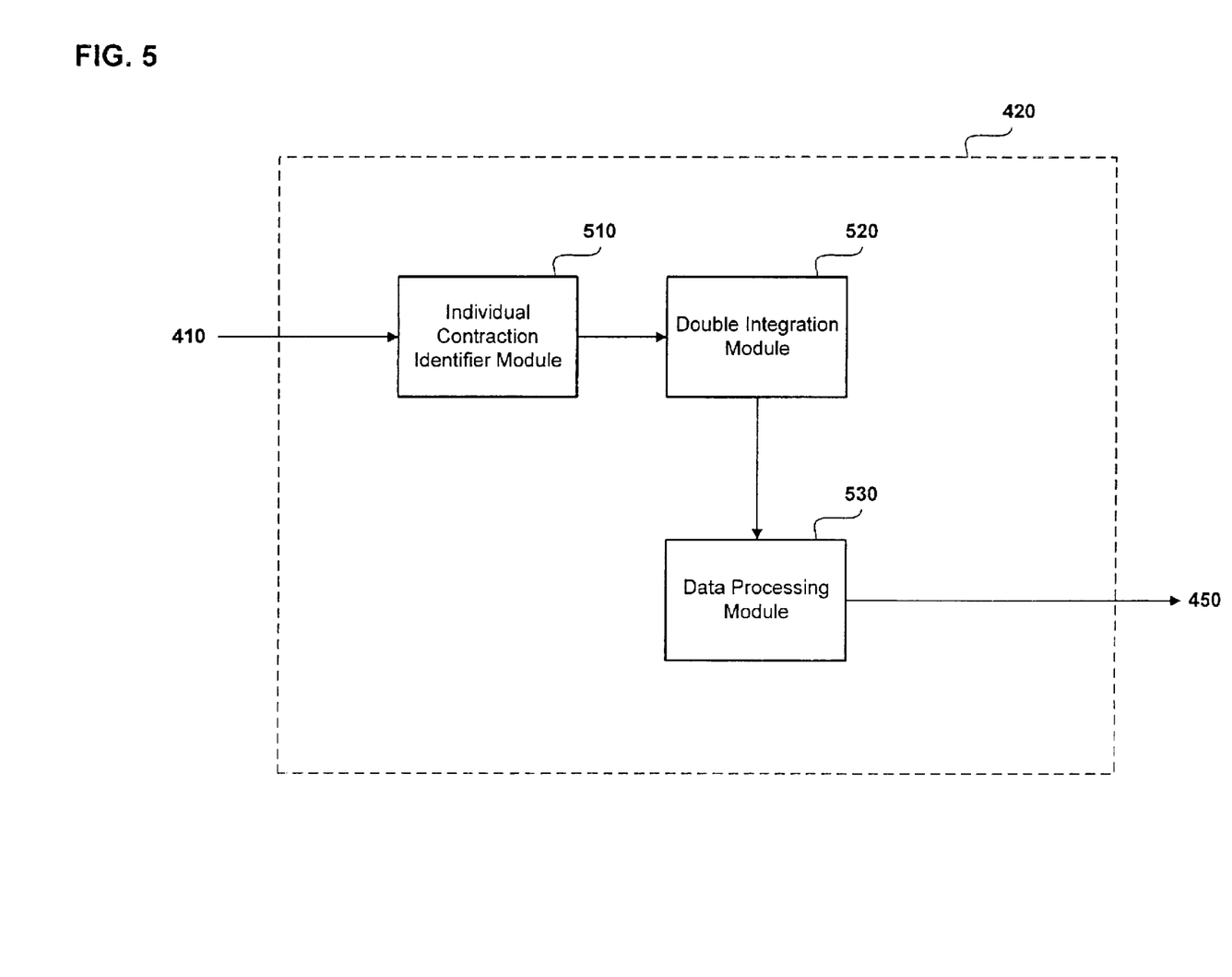
FIG. 5 is a block diagram showing further details of the components of the device of FIG. 4.

FIG. 5 shows the modules that may comprise the accelerometer data processing module 420. Generally, these modules include an individual contraction identifier module 510, a multiple integration module 520, and a data processing module 530. The individual contraction identifier module 510 identifies and segregates data corresponding to individual contractions of the heart. This module 530 can take many forms, as are well known in the art. For example, the module 530 may be set to search for the individual R or P waves of each heart contraction.

Once the individual contraction identifier module 510 has identified data from one or more individual heart contractions, the multiple integration module 520 manipulates the data. The signals provided by the acceleration sensor units 344 and 346 represent the acceleration of the portion of the heart in which each sensor is embedded or coupled. Because acceleration is known, displacement, or the difference in position of each portion of the heart from a beginning point to an ending point, can be identified based on the following Equations 1 and 2.

$$v(t) = \int a(t)dt \quad (1)$$

$$x(t) = \int v(t)dt \quad (2)$$

As illustrated by Equations 1 and 2, integrating acceleration, a(t), provides velocity, v(t), and integrating velocity provides displacement, x(t). Therefore, the multiple integration module 520 integrates the acceleration data measured by the acceleration sensor units, in the example embodiment twice, to identify the actual displacement, or movement, of the portion of the heart near the accelerometers. The integrations can be accomplished using a variety of known techniques. For example, digital filtering algorithms such as rectangular or trapezoidal summation may be used.

Figure 6:
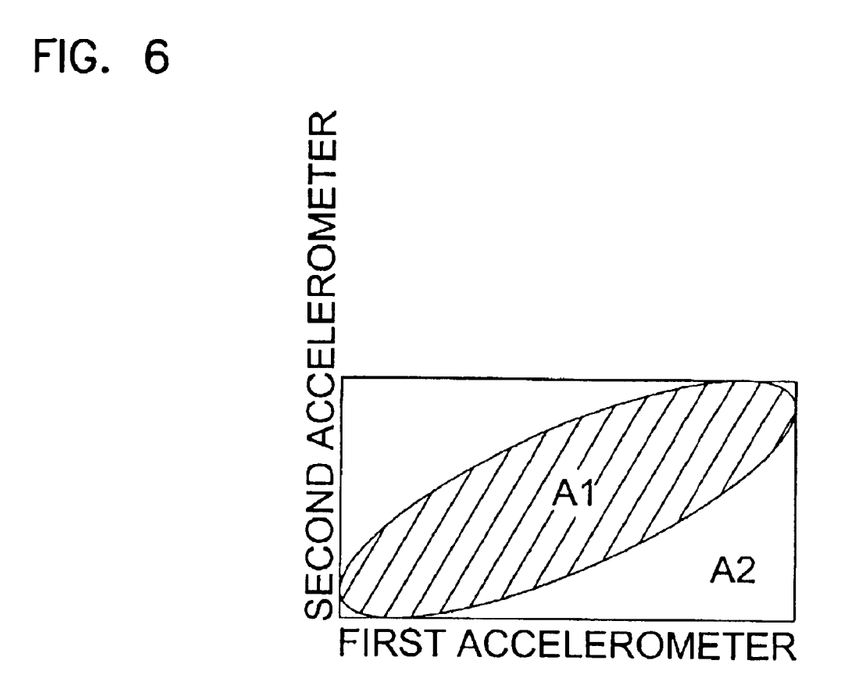
FIG. 6 is a graph of first accelerometer displacement data plotted against second accelerometer displacement data to form a displacement loop with area A1, as well as a normalized rectangle with area A2.

Once displacement of each accelerometer has been calculated, the data processing module 530 of the accelerometer data processing module 420 further manipulates the data to create a displacement loop and a synchronicity index. The displacement loop, as illustrated in FIG. 6, is a plot of the displacement of the first accelerometer plotted against the displacement of the second accelerometer during a cardiac cycle. An area A1 is the area inside the displacement loop. The displacement loop is normalized by enclosing the displacement loop by a rectangle of area A2.

The size of the displacement loop, or area A1, varies depending upon the patient. A displacement loop of a healthy individual would be a line or a small loop. An individual with asynchronous contraction would have an oval displacement loop (as shown). The more asynchronous the contraction of an individual's heart, the larger, or more rounded, the displacement loop.

The data processing module 530 may then calculate the synchronicity index as follows in Equation 3.

$$\text{Synchronicity Index} = A1/A2 \quad (3)$$

The synchronicity index is a measure of the phase difference of contraction at the two different locations of the heart where the acceleration sensor units are placed. The synchronicity indexes for a plurality of heart contractions may be calculated and averaged. For example, the device 300 may be set to measure a certain number of contractions, such as 30, and then average the synchronicity indexes calculated for each contraction. Alternatively, the device 300 may be set to measure contractions for a predetermined time period and then calculate the synchronicity indexes.

The smaller the synchronicity index is, the better the synchronicity of the contraction. A synchronicity index that is larger than the threshold described above indicates asynchronous contraction and, therefore, a possible candidate for CRT.

Figure 7:
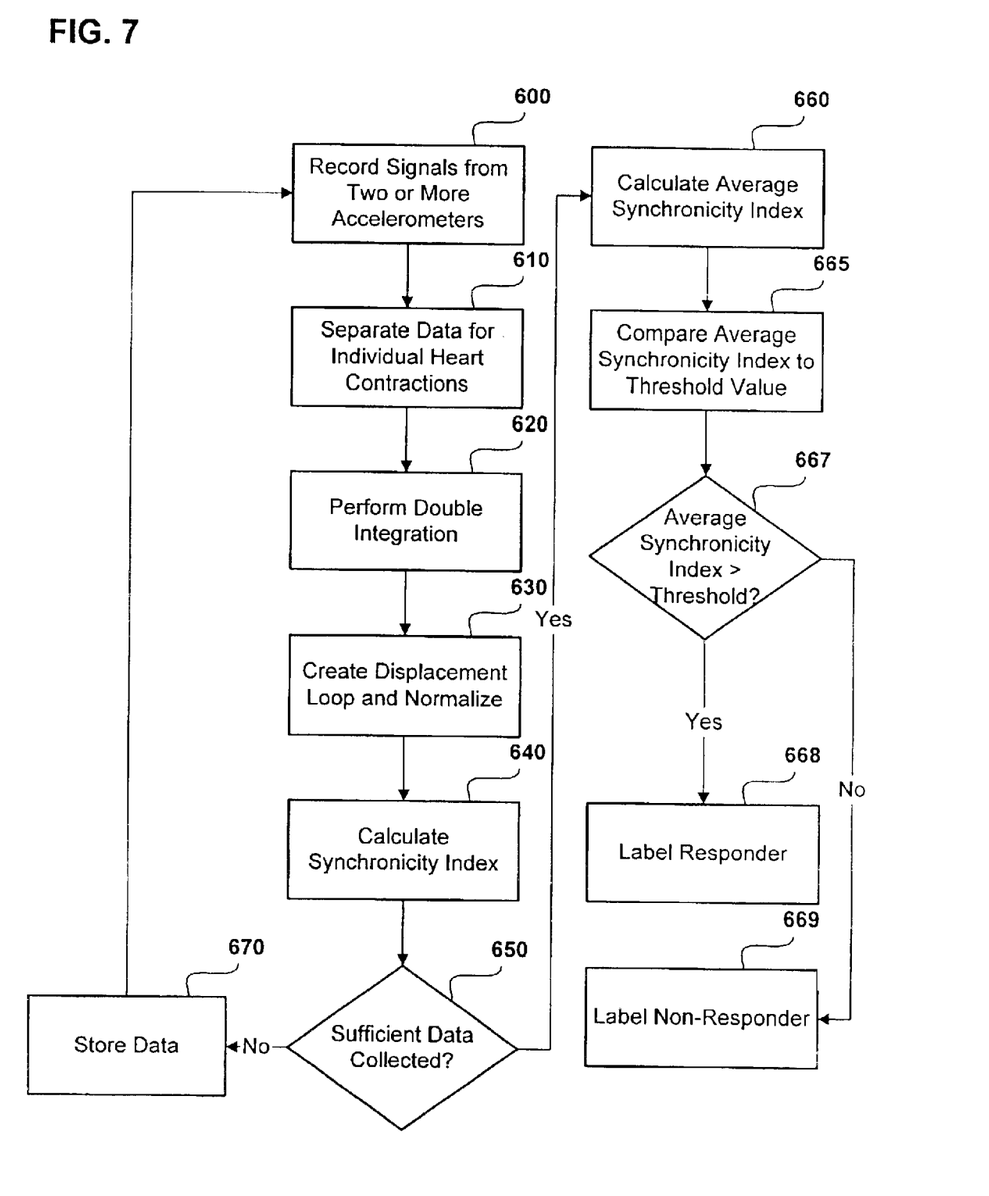
FIG. 7 is a flowchart depicting example logical operations for detecting synchronicity of different portions of a heart during contraction in accordance with the present invention.

The logical operations that may be performed by the device 300 are illustrated in FIG. 7. Initially, in operation 600, the acceleration sensor units 344 and 346 are used to measure the acceleration of the heart at two wall locations. For example, if the individual has a left bundle branch block, then operation 600 might accept signals from at least the acceleration sensor unit 346 positioned in the left ventricle free wall and unit 344 positioned in the interventricular septum so that two opposite walls responsible for left ventricular contraction may be monitored. It may also be desirable to monitor the right ventricular free wall with an additional accelerometer sensor unit implanted therein, such as when a right bundle branch block exists or when attempting to synchronize contraction of both the left and right ventricular free walls. As indicated, more than two sites may also be used, as well as atrial placements.

Next, control is passed to operation 610, in which data is separated for each individual heart contraction, as described above in reference to the individual contraction identifier module 510. Once acceleration data for a single heart contraction is identified, control is passed to operation 620, in which the multiple integration module 520 integrates the data twice to get displacement data.

Once displacement data is calculated, control is passed to operation 630, in which a displacement loop is created, such as by the data processing module 530. The displacement loop, as described above, provides a value for the area A1. In addition, the displacement loop is normalized, providing a value for the area A2. Control is then passed to operation 640, in which the data processing module 530 calculates the synchronicity index using Equation 3 above.

Next, in decisional operation 650, the device 300 determines whether sufficient data has been collected to label the individual as a responder or non-responder to CRT. As explained above, this determination can be made based on the number of contractions measured, the duration of time elapsed, or using other factors. If sufficient data has not been collected, control is passed to logical operation 670, in which the calculated synchronicity index, as well as possibly other data, such as acceleration and displacement data, are stored in memory, such as the memory module 440. Data collection may then continue.

If sufficient data has been collected, control is passed to logical operation 660, in which the device 300 calculates an average synchronicity index based on the plurality of synchronicity indexes calculated from the plurality of heart contractions measured. Then, in operation 665, the comparator module 430 compares the average synchronicity index to a threshold value. Control is then passed to decisional operation 667, in which it is determined whether the average synchronicity index is greater or less than the threshold value. If the average synchronicity index is greater, control is passed to operation 668, and the output module 450 indicates that the individual would be a responder to CRT. Alternatively, if the average synchronicity index is less than or equal to the threshold value, control is passed to operation 669, and the output module 450 indicates that the individual would not be a responder to CRT.

The device 300 may be used as an external, standalone apparatus to measure a patient's receptivity to CRT. If the device 300 is used externally, it may be necessary to introduce two or more of the accelerometers into or adjacent the heart, as described above, to measure the mechanical movement of the patient's heart. Alternatively, the device 300 may be implemented in an implantable CRT device and used to determine whether a patient will be a responder or non-responder to CRT. Such a system is shown and described with reference to FIG. 8 below.

Figure 8:
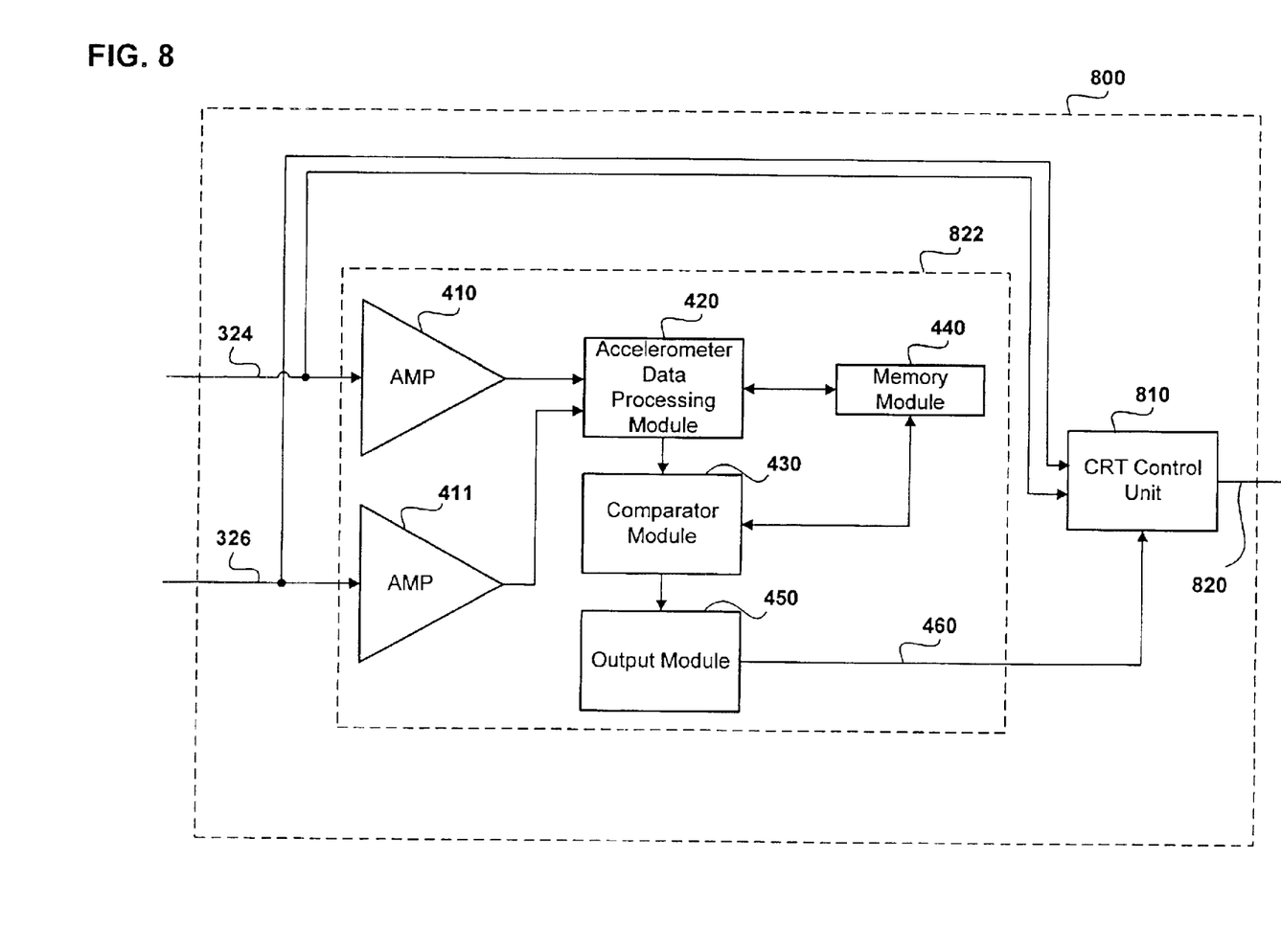
FIG. 8 is a block diagram depicting the primary components of a second example embodiment of a device in accordance with the present invention.

An alternative embodiment including an example of the present invention is shown in FIG. 8. In this embodiment, a simplified CRT device 800 is provided. The CRT device 800 provides CRT to a patient. The CRT device 800 includes a CRT control unit 810 coupled to an output lead 820. In addition, the CRT device 800 includes a control unit 822 including all of the modules used to implement an embodiment of the present invention, such as those described with reference to the control unit 322 of the example device 300. The leads 324 and 326 are coupled to the control unit 822, as described above, and are also coupled to the CRT control unit 810. Because the leads 324 and 326 include electrodes 350 and 352, the CRT control unit 810 may utilize the leads to sense the electrical activity within the heart. The output lead 820 of the CRT device 800 may be coupled to the heart to provide CRT to the heart. Conversely, the therapy may be provided via the leads 324 and 326.

The control unit 822 functions in a manner similar to that of the control unit 322 described above, except that the output 460 is coupled to the CRT control unit 810 of the CRT device 800. If CRT is not currently being administered and the control unit 822 determines that the individual is a responder to CRT, the control unit 822 can send a signal to the CRT control unit 810 to initiate CRT. Therefore, the CRT device 800, with the unit 822, can automatically determine whether an individual would be a responder to CRT and based on that determination initiate CRT.

The logical operations for detecting the difference between the accelerometer signals and for determining whether an individual would be a responder to CRT may be performed by a device other than the example external or implantable devices 300 and 800. For example, an external device programmer, communicating via telemetry, may be used. Furthermore, the logical operations may be implemented (1) as a sequence of computer implemented steps running on a computer system, and/or (2) as interconnected machine modules.

This implementation is a matter of choice dependent on the performance requirements of the devices 300 and 800 or device programmer implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A device for measuring a synchronicity of contraction of a heart to determine if an individual would be a responder to cardiac resynchronization therapy, the device comprising:

a first electrode adapted to be positioned at a first ventricular wall location and configured to mechanically measure movement of the first ventricular wall location;

a second electrode adapted to be positioned at a second ventricular wall location and configured to mechanically measure movement of the second ventricular wall location;

a processing module coupled to the first and second electrodes, the processing module adapted to process a first signal produced by the first electrode at the first ventricular wall location and a second signal produced by the second electrode at the second ventricular wall location and generate an output based on the processed signals; and a comparator module coupled to the processing module to indicate that the individual would be a responder if the output of the processing module exceeds a threshold and to indicate that the individual would be a non-responder if the output of the processing module is below the threshold.

2. The device of claim 1, wherein the first electrode includes a first accelerometer and the second electrode includes a second accelerometer.

3. The device of claim 1, wherein the processing module further comprises:

an integrator module that integrates the first signal and the second signal and plots the integrated first and second signals to form a displacement loop; and a synchronicity index module that measures a phase difference of contraction based on the displacement loop.

4. A device for determining whether an individual would be a responder to cardiac resynchronization therapy, the device comprising:

a first accelerometer adapted to be positioned at a first ventricular wall location;

a second accelerometer adapted to be positioned at a second ventricular wall location;

a processing module coupled to the first and second accelerometers, the processing module adapted to process a first signal produced by acceleration of the first accelerometer at the first ventricular wall location and a second signal produced by acceleration of the second accelerometer at the second ventricular wall location and generate an output; and a comparator module coupled to the processing module to indicate that the individual would be a responder if the output of the processing module exceeds a threshold and to indicate that the individual would be a non-responder if the output of the processing module is below the threshold.

5. The device of claim 4, wherein the processing module and the comparator module of the device are in vitro.

6. The device of claim 4, wherein the entire device is implanted into the individual.

7. The device of claim 4, wherein the processing module further comprises:

an integrator module that integrates the first signal and the second signal and plots the integrated first and second signals to form a displacement loop; and a synchronicity index module that measures a phase difference of contraction by normalizing the displacement loop.

8. A cardiac resynchronization system comprising:

a cardiac resynchronization device adapted to be coupled to a heart of an individual to provide cardiac resynchronization therapy; and a device coupled to the cardiac resynchronization device, the device including:
  a first accelerometer adapted to be positioned at a first ventricular wall location;
  a second accelerometer adapted to be positioned at a second ventricular wall location;
  a processing module coupled to the first and second accelerometers, the processing module adapted to process a first signal produced by acceleration of the first accelerometer at the first ventricular wall location and a second signal produced by acceleration of the second accelerometer at the second ventricular wall location and generate an output; and
  a comparator module coupled to the processing module to indicate that the individual would be a responder if the output of the processing module exceeds a threshold and to indicate that the individual would be a non-responder if the output of the processing module is below the threshold.

9. The cardiac resynchronization system of claim 8, wherein the processing module and the comparator module of the device are in vitro.

10. The cardiac resynchronization system of claim 8, wherein the device is implanted.

11. The cardiac resynchronization system of claim 8, wherein the cardiac resynchronization device and the device are a single unit.

12. The cardiac resynchronization system of claim 8, wherein the comparator is coupled to the cardiac resynchronization device to initiate cardiac resynchronization therapy if the individual is the responder.

13. A method for determining whether an individual would be a responder to cardiac resynchronization therapy, the method comprising steps of:

sensing acceleration with a first accelerometer located at a first location on the individual's heart to produce a first signal;

sensing acceleration with a second accelerometer located at a second location on the heart to produce a second signal;

processing the first signal and the second signal to create a synchronicity index that measures a phase difference of contraction at the first and second locations; and comparing the synchronicity index to a threshold to determine whether an individual would be a responder to cardiac resynchronization therapy.

14. The method of claim 13, wherein the processing step comprises steps of:

integrating the first and second signals to create integrated first and second signals;

plotting the integrated first and second signals to form a displacement loop; and normalizing the displacement loop to create the synchronicity index.

15. The method of claim 13, further comprising steps of:

selecting the first location as a portion of a ventricular free wall of the heart; and selecting the second location as a portion of an interventricular septum of the heart.

16. A device for determining whether an individual's heart would be a responder to cardiac resynchronization therapy, the device comprising:

a first accelerometer means for measuring acceleration of the heart at a first ventricular wall location and for producing a first signal;

a second accelerometer means for measuring acceleration of the heart at a second ventricular wall location and for producing a second signal;

a processing means for processing the first signal and the second signal and generating an output; and a comparator means for indicating whether the individual would be a responder or a non-responder to cardiac resynchronization therapy based on the output from the processing means.

17. The device of claim 16, wherein the processing means comprises:

means for amplifying and filtering the first and second signals;

a multiple integration means for integrating the first and second signals;

a displacement loop means for plotting a displacement loop based on the integrated signals;

a normalizing means for normalizing the displacement loop; and a synchronicity index means for measuring a phase difference of contraction based on the displacement loop.

18. A computer-readable medium having computer-executable modules comprising:

a processing module adapted to process a first signal produced by acceleration of a first accelerometer at a first ventricular wall location and a second signal produced by acceleration of a second accelerometer at the second ventricular wall location and generate an output; and a comparator module coupled to the processing module to generate a signal indicating that the individual would be a responder to cardiac resynchronization therapy if the output of the processing module exceeds a threshold and indicating that the individual would be a non-responder if the output of the processing module is below the threshold.

* * * * *